United States Patent [19]

Caldecourt et al.

[11] 4,335,308
[45] Jun. 15, 1982

[54] INSPECTION OF UNDERWATER STRUCTURES

[75] Inventors: Leonard R. Caldecourt, Faringdon; Gordon V. Evans, Blewbury; Tony V. Parsons, Didcot, all of England

[73] Assignee: United Kingdom Atomic Energy Authority, London, England

[21] Appl. No.: 110,406

[22] Filed: Jan. 8, 1980

[30] Foreign Application Priority Data

Jan. 10, 1979 [GB] United Kingdom ................. 7900845

[51] Int. Cl.³ .......................................... G01N 23/00
[52] U.S. Cl. ............................. 250/358 R; 250/358 P
[58] Field of Search ........... 250/256, 308, 357, 358 R, 250/358 P

[56] References Cited

U.S. PATENT DOCUMENTS

| 2,968,728 | 1/1961 | Eberline | 250/256 |
| 2,978,581 | 4/1961 | Wehrli | 250/357 |
| 3,263,077 | 7/1966 | Brunton et al. | 250/357 |
| 3,432,656 | 3/1969 | Smith et al. | 250/358 R |

Primary Examiner—Alfred E. Smith
Assistant Examiner—Janice A. Howell
Attorney, Agent, or Firm—Larson and Taylor

[57] ABSTRACT

A radiation detector for use in an underwater environment, comprising a radiation detector tube having a metal case out of one end of which extends an output lead wherein the said end of the tube is encased in a resilient water-proof compound so as to prevent the ingress of water into the body of the radiation detector tube. Marine structures incorporating such radiation detectors also are described.

11 Claims, 4 Drawing Figures

INSPECTION OF UNDERWATER STRUCTURES

The present invention relates to the inspection of the underwater parts of marine structures, and in particular to the inspection of offshore oil and gas platform structures.

It is well established that the integrity of metal structures can be investigated by techniques which involve the irradiation of the structure with one or more forms of high energy radiation and the detection and measurement of radiation which is transmitted through or backscattered from the components of the structure under test. Such techniques are now being applied to structures such as offshore oil or gas platform structures. A particularly important type of inspection is so-called grout monitoring.

Platforms for use in the recovery of oil or gas from offshore fields often have legs which are attached to piles which are inserted into holes drilled in the sea bed, and then secured in position by means of a cement slurry, known as grout, which is pumped down the piles, which are made hollow for that purpose. It is of the utmost importance that the grout should fill the cavity surrounding the pile, and that it should be of adequate density.

One way in which the first of these parameters can be monitored is to attach radiation detectors to strategic points of a given platform structure and add a radioactive tracer material to the grout so that as it reaches each of the monitored points its presence can be measured. The density of the grout can be measured by means of an adaptation of a nuclear radiation transmission technique. The problem with putting such methods into practice is providing radiation detectors which are capable of withstanding the high pressures and arduous marine conditions in which such structures are built and used.

In one aspect of the present invention there is provided a radiation detector for use in an underwater environment, comprising a radiation detector tube having an hermetically sealed metal case out of one end of which extends an output lead, wherein the said end of the radiation detector tube and the output lead are encapsulated in a resilient impervious material so as to prevent the ingress of water to the part of the radiation detector tube where the output lead emerges.

According to the invention in another aspect there is provided a structure for use in a marine environment having at least one position at which it is desired to detect the presence or measure the density of a cement grout, a radiation detector tube which has an hermetically sealed metal case out of one end of which extends an output lead, wherein the said end of the radiation detector tube and the output lead are encapsulated in a resilient impervious compound so as to prevent the ingress of water to the part of the radiation detector tube where the output lead emerges, and a telemetry cable connecting the radiation detector to a recording station.

Preferably, the radiation detector tube is mounted in a robust sealed metal outer housing from which it is isolated mechanically by means of a plurality of resilient spacers, the outer housing including a waterproof plug and socket connection for a telemetry cable. The outer housing of the radiation detector can be provided with means whereby the radiation detector can be attached to the structure.

A suitable form of radiation detector tube is a Geiger-Müller counter, and a suitable resilient impervious compound is a resilient epoxy resin compound.

The invention will now be described, by way of example, with reference to the accompanying drawings, in which.

Figure 1:
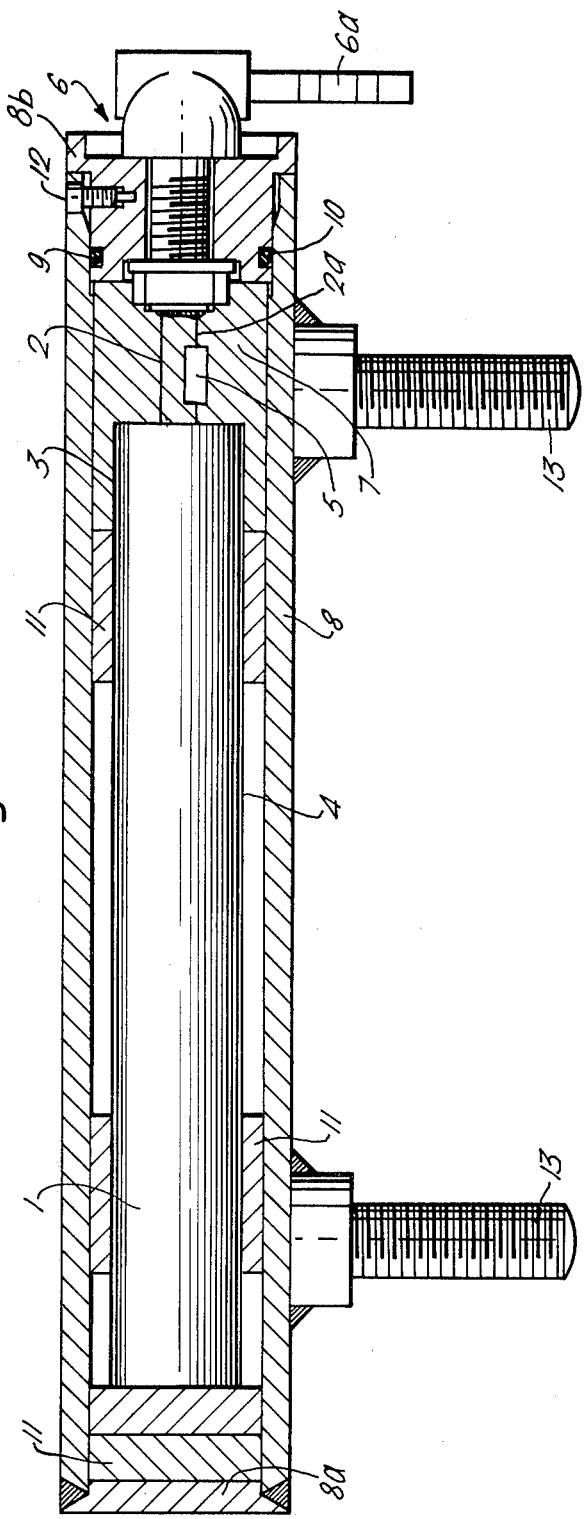
FIG. 1 is a longitudinal section of a radiation detector embodying the invention.

Referring to FIG. 1 of the drawings, a radiation detector assembly for use in an underwater environment consists of a metal cased Geiger-Müller tube 1 which has an output lead 2 projecting from one end 3 of the casing 4 of the Geiger-Müller tube 1. One wire 2a of the output lead includes a resistor 5. The output lead 2 terminates in a watertight plug and socket assembly 6 to which is attached a telemetry cable 6a. The end 3 of the casing 4 of the Geiger-Müller tube 1, the output lead 2, resistor 5 and female part of the watertight plug and socket assembly 6 are all encapsulated in a moulding 7 made of a resilient epoxy resin compound. The Geiger-Müller tube 1 is surrounded by a metal outer housing 8, one end of which is closed by an end plate 8a, and the other end of which is closed by means of an end plug 8b which incorporates the male portion of the watertight plug and socket assembly 6. The outer housing 8 is rendered watertight by means of an O-ring 9 which seats in a groove 10 formed in the outer surface of the end plug 8b. The Geiger-Müller tube 1 is positioned within, and mechanically isolated from, the outer housing 8 by means of resilient spacers 11. The end plug 8b is held in place by means of three grub screws 12 disposed regularly around the open end of the housing 8. The dimensions of the end plug 8b, the moulding 7 and the outer housing 8 are such that when the end plug is in position, the moulding 7 and the spacer 11 at the closed end of the outer housing 8 are under a degree of compression. This aids the sealing of the output lead 2 and the mechanical stabilisation of the Geiger-M/üller tube 1 within the outer housing 8. Two mounting studs 13 are welded to the outer housing 8.

The moulding 7 and the spacers 11 provide a resilient mounting for the Geiger-Müller tube 1 and effectively decouple the Geiger-Müller tube 1 from the outer housing 8 so as to provide vibration resistance. The resilience of the moulding 7 and the spacers 11 also enable them to accommodate distortions of the outer housing 8, whether these arise from pressure effects or mechanical shocks.

In an alternative form of the detector, which it is not thought necessary to illustrate in detail, the plug assembly 6 is such that the telemetry cable 6a emerges axially instead of at right angles to the longitudinal axis of the radiation detector, and the studs 13 are omitted. While this form is not illustrated in detail, it is shown schematically at 48 in FIG. 4, to be discussed below. Thus the radiation detector is in a form in which it can be raised or lowered by means of a cable which can either be the telemetry cable 6a if it is of a suitable type, or a separately attached cable.

Figure 2:
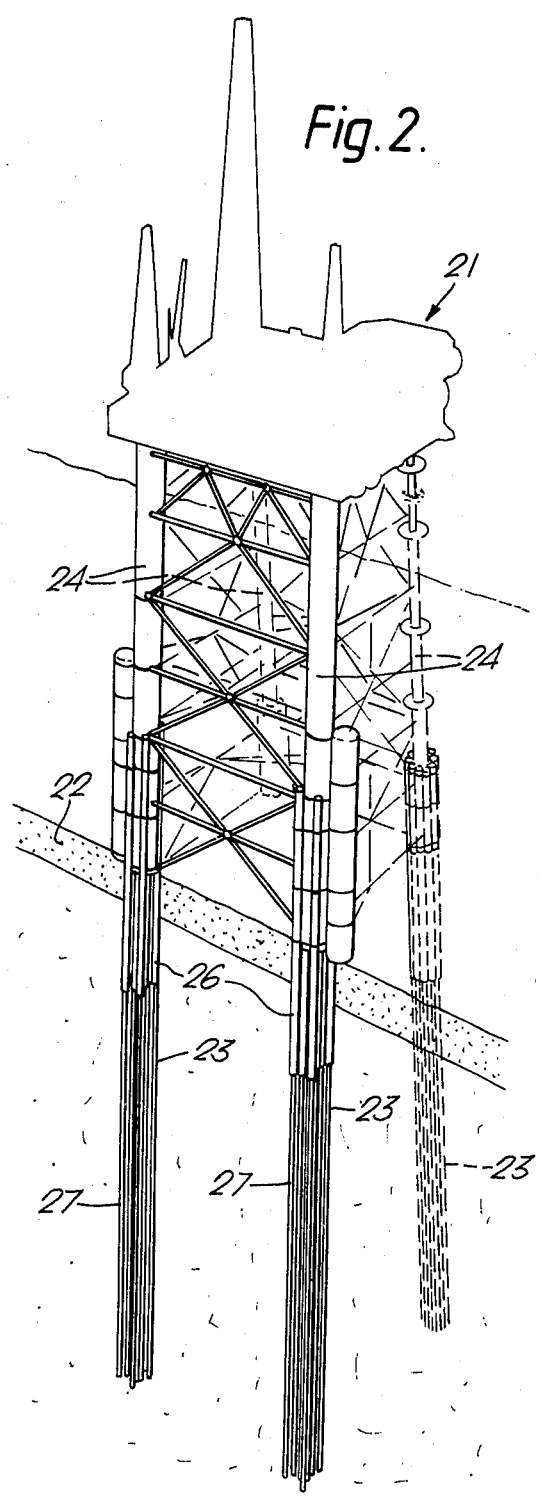
FIG. 2 is a general view of an offshore platform structure showing the positions of piles holding it to the sea bed.

Referring to FIG. 2, an offshore platform structure indicated generally by the reference numeral 21 is attached to the sea bed 22 by means of a plurality of piles 23 some of which are attached to the outside of their respective legs 24 of the platform structure 21 and the others of which are passed down the insides of the legs 24 of the platform 21. Each of the piles 23 is in two parts, a first stage 25 which is surrounded by a pile sleeve 26, and a second stage 27 which is not surrounded by a sleeve.

Figure 3:
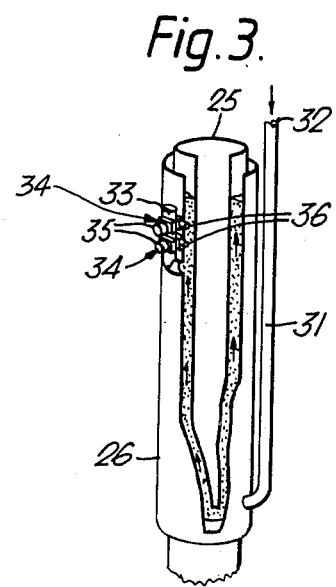
FIG. 3 shows a view of an arrangement for monitoring the density of cement grout surrounding a portion of a pile.

Referring to FIG. 3, which shows a portion of the first stage 25 of a pile 23 and a portion of its associated pile sleeve 26, the pile sleeve 26 has an inlet pipe 31 by means of which cement grout 32 can be pumped in to fill the annular gap between the first stage 25 of the pile 23 and the pile sleeve 26. At the top of the pile sleeve 26 is an outlet pipe 33 for excess grout 32. Attached to the outlet pipe 33 are two nuclear density gauges 34 each of which consists of a γ-ray source 35 on one side of the outlet pipe 33 and a radiation detector 36, such as that described with reference to FIG. 1, attached to the outlet pipe 33 diametrically opposite the radiation source 35. The radiation sources 35 are of a known intensity, therefore the measured intensity of the radiation traversing the grout 32 flowing through the outlet pipe 33 is a measure of the density of the grout 32.

Figure 4:
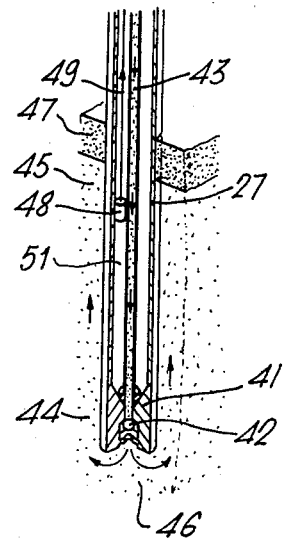
FIG. 4 shows an arrangement for monitoring the movement of cement grout during its emplacement around another portion of a pile.

FIG. 4 shows the lower end of a second stage 27 of a pile 23. The lower end 41 of the second stage 27 of the pile 22 is closed off but for a centrally located non-return valve 42 which communicates with a central grout supply tube 43. The pile 23 is inserted into a hole 44 which is drilled in the sea bed. Cement grout 45 which is forced down the supply tube 43 passes out of the non-return valve 42 and fills up the gap 46 between the pile 23 and the hole in the sea bed, pushing before it a layer of drilling mud 47. A radiation detector 48 similar to that described with reference to FIG. 1 except that it does not have the mounting studs 13 and the plug assembly 6 is such that the telemetry cable 6a emerges axially is suspended in the gap 51 by means of a cable 49 which can incorporate the telemetry cable 6a. A radioactive tracer such as scandium is mixed with the grout 45 so that as the radiation detector 48 becomes immersed by the rising grout 45, this fact is detected and suitably recorded by a recording station on the upper portion of the platform structure 21. The radiation detector 48 is then withdrawn a short distance and the process is repeated. If the cable 49 is calibrated, a direct measure of the position of the surface of the grout 45 can be obtained.

We claim:

1. A radiation detector for use in a deep water offshore underwater environment, comprising a hermetically sealed outer casing having a waterproof plug and socket connection for a telemetry cable, and within the outer casing, a radiation detector tube having a hermetically sealed metal case out of one end of which extends an output lead, wherein the said end of the radiation detector tube through which the output lead passes, the output lead and a portion of the plug connected to the output end are encapsulated in a resilient impervious material so as to prevent the ingress of water to the part of the radiation detector tube where the output lead emerges, and means for mechanically isolating the radiation detector tube from the outer casing.

2. A radiation detector device according to claim 1 wherein the means for isolating the radiation detector tube from the outer casing comprises a plurality of resilient spacers, the encapsulation around the output lead end of the radiation detector tube forming one of the said spacers.

3. A radiation detector according to claim 1, wherein the radiation detector tube is a Geiger-Müller counter tube.

4. A radiation detector according to claim 1, wherein the resilient impervious material is a resilient epoxy resin compound.

5. A radiation detector according to claim 1, incorporated into an off-shore exploration structure.

6. A structure for use in an off-shore exploration structure having at least one position at which it is desired to detect the presence or measure the density of a cement grout, a radiation detector positioned at that point, said radiation detector comprising a hermetically sealed outer casing having a waterproof plug and socket connection for a telemetry cable, and within the outer casing, a radiation detector tube having a hermetically sealed metal case out of one end of which extends an output lead, wherein the said end of the radiation detector tube through which the output lead passes, the output lead and a portion of the plug connected to the output end are encapsulated in a resilient impervious material so as to prevent the ingress of water to the part of the radiation detector tube where the output lead emerges, and means for mechanically isolating the radiation detector tube from the outer casing, a measuring station and a telemetry link connecting the radiation detector to the measuring station.

7. A structure according to claim 6, wherein a radiation detector is positioned opposite a source of penetrating radiation of known intensity so as to measure the density of the grout by means of the decrease in intensity of the radiation traversing a known thickness of the grout.

8. A structure according to claim 6 including at least one radiation detector positioned to sense when the surface of the grout reaches it, the grout having been rendered radioactive.

9. A structure according to any one of claims 6, 7 or 8, wherein the radiation detector tube is a Geiger-Müller counter tube.

10. A structure according to any one of claims 6, 7 or 8, wherein the resin impervious material is a resilient epoxy resin compound.

11. A structure according to any one of claims 6, 7 or 8, wherein the means for isolating the radiation detector tube from the outer casing comprises a plurality of resilient spacers, the encapsulation around the output lead end of the radiation detector tube forming one of the said spacers.

* * * * *